United States Patent [19]
Kagawa et al.

[11] Patent Number: 6,046,168
[45] Date of Patent: *Apr. 4, 2000

[54] PEPTIDE INHIBITS BLOOD TRIGLYCERIDE LEVEL

[75] Inventors: Kyoichi Kagawa; Chizuko Fukuhama; Hisako Matsutaka, all of Osaka; Toyoo Nakamura, Ibaraki; Masahiro Numata, Ibaraki; Shigeaki Watanabe, Ibaraki; Kazuhisa Honda, Ibaraki, all of Japan

[73] Assignees: Hankyu-Kyoei Bussan Co., Ltd., Osaka; Itoham Foods, Inc., Hyodo, both of Japan

[*] Notice: This patent is subject to a terminal disclaimer.

[21] Appl. No.: 08/981,384

[22] PCT Filed: Jun. 23, 1995

[86] PCT No.: PCT/JP95/01264

§ 371 Date: Dec. 23, 1997

§ 102(e) Date: Dec. 23, 1997

[87] PCT Pub. No.: WO97/00890

PCT Pub. Date: Jan. 9, 1997

Related U.S. Application Data

[63] Continuation-in-part of application No. 08/525,515, filed as application No. PCT/JP94/00297, Feb. 24, 1994, Pat. No. 5,756,467.

[30] Foreign Application Priority Data

Mar. 24, 1993 [JP] Japan .................................. 5-065643

[51] Int. Cl.$^7$ ................................ C07K 5/08; C07K 7/06; A61K 38/06; A61K 38/08
[52] U.S. Cl. .............................. 514/16; 514/18; 530/329; 530/331; 424/439; 426/656; 435/71.1
[58] Field of Search ..................... 530/329, 331; 514/16, 18; 424/439; 426/656; 435/71.1

[56] References Cited

U.S. PATENT DOCUMENTS 5,723,443  3/1998  Kagawa et al. .......................... 514/18
5,756,467  5/1998  Kagawa et al. .......................... 514/18

FOREIGN PATENT DOCUMENTS

| 6 115494 | 10/1994 | Australia . |
| WO 8906970 | 8/1989 | Japan . |
| 3-167199 | 7/1991 | Japan . |
| 7-188284 | 7/1995 | Japan . |

OTHER PUBLICATIONS

Karelin et al., Biochem. Biophys. Res. Commun. vol. 202 No. 1 (Jul. 15, 1994) pp. 410–415.

WPIDS Abstract No. 91–084519 of JP 03031298, Feb. 1991.

English Absrtact of JP 3–167199, Jul. 1991.

*Primary Examiner*—Bennett Celsa
*Attorney, Agent, or Firm*—Davidson, Davidson & Kappel, LLC

[57] ABSTRACT

The present invention relates to a peptide having the amino acid sequence shown in the sequence listing; an agent for inhibiting elevations of triglyceride levels in blood comprising the above peptide, a peptide Val-Tyr-Pro and/or a peptide Val-Thr-Leu as an active component; a food for specified health use which is endowed with a function of inhibiting elevations of triglyceride levels in blood by comprising these peptides as an active component; and a feed which is endowed with a function of inhibiting elevations of triglyceride levels in blood by comprising these peptides as an active component. According to the present invention, it becomes possible to prevent or treat obesity and hyperlipemia in humans and animals as well as cardiovascular diseases such as hypertension and arteriosclerosis associated therewith. Furthermore, it becomes possible to improve the meat quality of livestock and hatchery fish.

11 Claims, 3 Drawing Sheets

FIG.1

Gel Filtration Chromatogram of Globin Proteolysate

FIG.2

Reversed Phase (Acidic) Chromatogram of Globin Proteolysate

FIG.3

Reversed Phase (Neutral) Chromatogram

PEPTIDE INHIBITS BLOOD TRIGLYCERIDE LEVEL

This application is a CIP of Ser. No. 08/525,515 (Sep. 25, 1995) now U.S. Pat. No. 5,756,467; which was a Section 371 PCT/JP94/00297 (Feb. 24, 1994).

TECHNICAL FIELD

The present invention relates to a novel peptide inhibiting elevations of triglyceride levels in blood; an agent for inhibiting elevations of triglyceride levels in blood comprising the peptide as an active component; a food for specified health use (the so-called physiologically functional food) endowed with a function of inhibiting elevations of triglyceride levels in blood; and a feed endowed with a function of inhibiting elevations of triglyceride levels in blood.

By administering the agent of the invention inhibiting elevations of triglyceride levels in blood to thereby clean fatty blood, it becomes possible to prevent or treat obesity and hyperlipemia in humans and animals as well as cardiovascular diseases such as hypertension and arteriosclerosis associated therewith. Furthermore, it becomes possible to improve the meat quality of livestock and hatchery fish.

BACKGROUND ART

Excessive intake of fat and sugar is known to cause obesity, hyperlipemia and the like. Elevations of triglyceride (hereinafter, sometimes referred to as "TG") levels in blood in hyperlipemia are said to become a cause which brings disorders such as hypertension and arteriosclerosis. Then, a number of attempts to inhibit elevations of TG levels in blood have been made to improve obesity and hyperlipemia.

At present, in order to inhibit elevations of TG levels in blood, dietary restriction, intake of dietary foods (such as fibers) and administration of various pharmaceuticals are carried out. As such pharmaceuticals, dextran sulfate which enhances lipoprotein lipase activity in blood, nicomol which inhibits lipid absorption, clofibrate and pravastatin which are lipid metabolism improving agents, and the like are used.

However, dietary restriction gives pain to those who practice it and side effects caused by the administration of the above pharmaceuticals are also apprehended. Thus, development of an agent for inhibiting elevations of blood TG levels is desired which has a stronger effect of inhibiting elevations of blood TG levels and in which there is no apprehension about causing side effects.

On the other hand, at present, concentrated feeds are given to livestock and hatchery fish for promoting their growth. As a result, abnormalities in fat metabolism occur also in such livestock and fish, and TG levels in their blood tend to elevate. Due to these elevations of TG levels in blood, fat contents in livestock and hatchery fish become excessive. Thus, eating such livestock or fish leads to excessive fat intake. Furthermore, such livestock and fish have gradually failed to meet consumers' liking in taste. In addition, the increase in fat contents described above is a serious issue relating to a problem of waste of feeds and also relating to a problem of disposal of the fat attached to slaughtered bodies. Thus, inhibition of elevations of TG levels in blood is an urgent need, in particular, in the stockbreeding industry and the fisheries industry in Japan.

Recently, a patent application has been filed for an oligopeptide-containing material developed by some researchers including one of the present inventors (International Publication No. WO89/06970), and a technology similar to this is disclosed in Japanese Unexamined Patent Publication No. 2-154693.

Also, it has been made clear that specific oligopeptides have lipid metabolism improving effects including inhibition of elevations in blood TG levels Kyoichi Kagawa, Food Chemical Monthly, Vol. 6, No. 2, p. 80–84 (1990); Chizuko Fukuhama et al., FOLIA PHARMACOLOGICA JAPONICA, Vol. 97, p.38 (1991).

DISCLOSURE OF THE INVENTION

The oligopeptide-containing materials disclosed in the above patent publication, etc. are mixtures of proteolysates and, thus, amino acid sequences for their truly active components (i.e., peptides as their active components) have not yet been elucidated.

This suggests that the above peptide-containing materials are low in purity as pharmaceuticals. Further, when such a material is combined in a food, it is difficult to quantitatively determine the material separately from other peptides contained in the food and thus there occurs a problem of quality control.

Therefore, it is necessary to ascertain the truly active components in the above peptide-containing materials, i.e., the peptides inhibiting elevations of TG levels in blood as active components.

It is an object of the present invention to analyze amino acid sequences for the above-described peptides as active components. It is another object of the present invention to provide an agent for inhibiting elevations of triglyceride levels in blood comprising the above peptide(s) as an active component(s); a physiologically functional food endowed with a function of inhibiting elevations of triglyceride levels in blood; and a feed endowed with a function of inhibiting elevations of triglyceride levels in blood.

As a result of intensive and extensive researches toward the solution of the above assignments, the present inventors have found that the above assignments can be solved by the invention described below.

The subject matters of the present invention are as follows.

(1) A peptide having the amino acid sequence shown in SEQ ID NO: 1.

(2) An agent for inhibiting elevations of triglyceride levels in blood comprising a peptide having the amino acid sequence shown in SEQ ID NO: 1 and/or a peptide Val-Tyr-Pro and/or a peptide Val-Thr-Leu as an active component(s).

(3) A food for specified health use which is endowed with a function of inhibiting elevations of triglyceride levels in blood by comprising a peptide having the amino acid sequence shown in SEQ ID NO: 1 or said peptide in combination with a peptide Val-Tyr-Pro and/or a peptide Val-Thr-Leu as an active component(s).

(4) A feed which is endowed with a function of inhibiting elevations of triglyceride levels in blood by comprising a peptide having the amino acid sequence shown in SEQ ID NO: 1 or said peptide in combination with a peptide Val-Tyr-Pro and/or a peptide Val-Thr-Leu as an active component(s).

Hereinbelow, the present invention will be described in detail.

The peptide of the invention having the amino acid sequence shown in SEQ ID NO: 1 and the peptides Val-Tyr-Pro and Val-Thr-Leu which may be contained in the agent of the invention inhibiting elevations of triglyceride levels in blood as active components (hereinafter, referred to as "the peptide(s) of the invention") can be separated and purified from naturally occurring proteins. Alternatively, they can be chemically synthesized directly by conventional methods. It is also possible to prepare the peptide of the invention by engineering a gene having a base sequence corresponding to the above peptide sequence, inserting the gene into an appropriate expression vector, and expressing the gene in an appropriate host.

A. Hereinbelow, a method for separating and purifying the above peptides from naturally occurring proteins will be described.

As a starting material for preparing the peptide(s) of the invention, a wide variety of proteins may be used. For example, an animal protein such as fish meat protein, fish powder, globin, etc. or a plant protein such as wheat gluten, soybean cazein, etc. may be used.

Among these proteins, globin proteins such as hemoglobin and myoglobin are especially preferable in that they can strongly produce the desired effect of inhibiting elevations of TG levels in blood.

The kind of animal as a source of such globin protein is not particularly limited. Blood from bovine, porcine, sheep, human, equine, etc. may be used.

Then, the above-mentioned protein should be hydrolyzed. Operations for this hydrolysis are performed according to the method described in International Publication No. WO89/06970, supra. As a hydrolase used for the hydrolysis, one or more hydrolases selected from acid proteases, neutral proteases or alkaline proteases may be used.

Conditions, etc. to be employed in the hydrolysis of a globin protein are described below.

First, a globin protein-containing material is dispersed in water to give a solid content of 5–30% by weight. Then, the pH of this mixture is adjusted with acid or alkali to give an optimum pH for protease(s). Thereafter, protease(s) is(are) added to this mixture at once or gradually and reacted at 20–70° C. for 3–48 hours to thereby achieve hydrolysis.

Subsequently, the resultant proteolysate is dried and caked as it is or after adding thereto an appropriate amount of filler such as carboxymethyl cellulose or dextrin. Thus, a proteolysate having an effect of inhibiting elevations of TG levels in blood can be obtained.

This proteolysate contains the peptide(s) of the invention at least 0.1% by weight.

Subsequently, the enzyme-treated proteolysate of the invention is purified. For such purification, conventional purification processes may be employed.

For example, ion exchange, ultrafiltration, reversed phase chromatography, etc. may be combined appropriately to purify those fractions containing a desired peptide.

Although operations by means of ion exchange or ultrafiltration are not necessarily essential, it is preferable to incorporate them in the separation and purification process from the viewpoint that they can improve the degree of separation and purification.

Those fractions can be separated and purified by combining reversed phase chromatography under acidic conditions and that under neutral conditions. The amount of the desired peptide in a fraction can be determined by known methods for protein determination, e.g., the ninhydrin method.

The amino acid sequence for the thus selected fraction can be identified by known methods and thereby the presence of the peptide(s) of the invention can be confirmed.

The peptide(s) of the invention derived from the thus separated fraction can be used as an active component of an agent for inhibiting elevations of TG levels in blood.

Also, the fraction itself may be used directly as an active component of the above agent.

The peptide(s) of the invention may be synthesized chemically by conventional peptide synthesis methods. For example, the azide method, the acid chloride method, the acid anhydride method, the mixed acid anhydride method, the DCC method, the active ester method, the carboimidazol method, the oxidation-reduction method, the DCC-additive (HOMB, HOBt, HOSu) method (see, for example, Schreder & Luhke, *The Peptide,* Vol. 1, p.1–481 (1966), Academic Press, New York, USA; or Izukiya et al., *Peptide Synthesis,* Maruzen Co., Ltd., p.1–312 (1975)) and the like may be given.

Either solid phase synthesis or liquid phase synthesis may be employed in the peptide synthesis methods enumerated above.

In those peptide synthesis methods, amino acids having a side chain functional group such as tyrosine and threonine are preferably protected in their side chain functional groups. As a protective group, known protective groups such as a benzyloxycarbonyl group (Cbz-), t-butoxycarbonyl group (Boc-), benzyl group (Bz-), etc. may be used.

Deblocking of such a protective group can be performed during the process of synthesis of the peptide(s) of the invention by conventional methods.

B. An agent for inhibiting elevations of TG levels in blood can be prepared using the peptide(s) of the invention as an active component(s).

As a carrier for the agent for inhibiting elevations of TG levels in blood, those excipients (such as fillers, extenders, binders, moisturizing agents, disintegrating agents, surfactants) or diluents which are conventionally used in the preparation of formulations depending on the form of use of the formulation may be used. The form of a formulation is not particularly limited as long as the formulation effectively contains the peptide(s) of the invention. For example, the formulation may be in a form of a solid agent such as tablets, powder, granules, pills; or in a form of an injection agent such as solutions, suspensions and emulsions. Alternatively, the agent of the invention may take a form of a dry product which can be made into a liquid form upon addition of an appropriate carrier before use. Any of these forms may be prepared by conventional methods.

The dose of the thus obtained agent for inhibiting elevations of TG levels in blood is appropriately selected depending on the method and form of administration of the formulation, conditions of the patient who receive the formulation, etc.

Generally, a formulation containing the peptide(s) of the invention about 0.001 to 80% by weight is prepared and, preferably, the formulation is administered so that the amount of the peptide(s) of the invention administered is about 1 to 100 mg for one adult per day. The administration is not necessarily performed once a day. It may be performed 3 to 4 times a day.

The pharmaceutical formulations of various forms as described above may be administered through an appropriate administration route depending on the form. For example, the formulation in a form of an injection agent may be administered by intravenous, intramuscular, subcutaneous, intracutaneous, or intraperitoneal administration, etc. and the pharmaceutical formulation in a form of a solid agent may be administered by oral administration, etc.

C. A food for specified health use (the so-called physiologically functional food) endowed with a function of inhibiting elevations of TG levels in blood can be prepared by using the peptide(s) of the invention as an active component(s). And the peptide of the invention can be used as a food additive of general foods.

The kinds of the above food are not particularly limited. The health food may be applicable to milk, pudding, curry, hash, stew, meat sauce, ham, cake, chocolate and the like.

In particular, milk is preferable since it can facilitate the intake of the peptide(s) of the invention which is(are) difficult for infants to take directly because of the tastes thereof. Also, the addition of the peptide(s) of the invention to foods such as cake and chocolate which essentially promote obesity is desirable from the viewpoint that obesity to be caused by the intake of the above foods can be prevented.

The amount of the peptide(s) of the invention added to the physiologically functional food is appropriately selected depending on the kind of the food, the purpose of addition, the effect expected to be produced by the intake of the food, etc.

Generally, it is preferable to allow the food to contain the peptide(s) of the invention so that about 0.1 to 4 mg of the peptide(s) of the invention can be taken per one meal.

D. A feed endowed with a function of inhibiting elevations of TG levels in blood of livestock, etc. can be prepared by combining with a feed the peptide(s) of the invention as an active component(s).

The feed with which the peptide(s) of the invention is(are) combined may be either a feed for livestock such as cows, pigs, chickens, etc. or a feed for hatchery fish such as sea breams, young yellowtails, etc.

The amount of the peptide(s) of the invention combined in a feed is appropriately selected depending on the kind of the feed, the effect expected to be produced by the intake of the feed, etc.

Generally, it is preferable that the peptide(s) of the invention be combined in a feed at a rate of 0.1 to 4% by weight.

DETAILED DESCRIPTION OF THE PREFERRED EMBODIMENTS

The present invention will be described more specifically below with reference to the following Examples, etc., which should not be construed as limiting the technical scope of the present invention.

REFERENCE EXAMPLE

Preparation of A Globin Proteolysate

Figure 1:
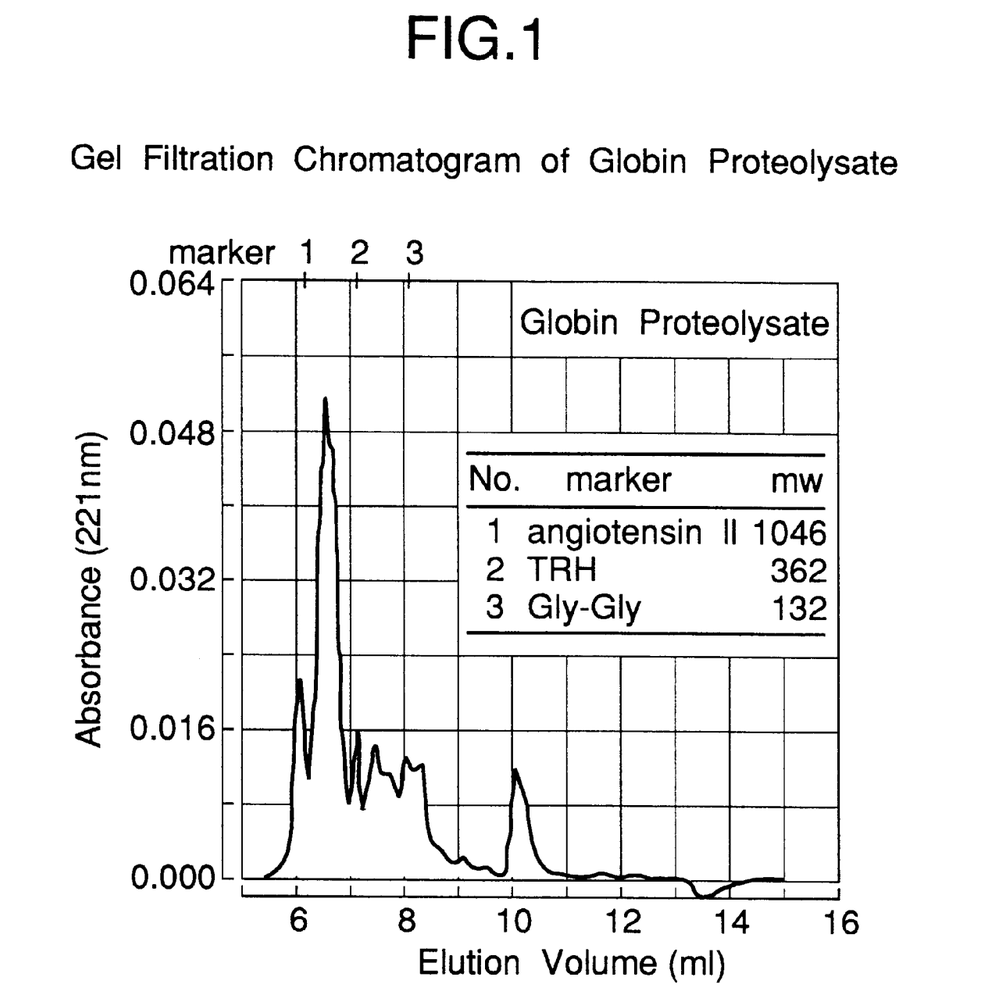
FIG. 1 is a gel chromatogram of a globin proteolysate.

A method of preparation of a globin proteolysate using bovine erythrocytes will be described below in detail. The molecular weight distribution of the resultant globin proteolysate was examined by gel filtration chromatography (FIG. 1).

The gel filtration chromatography was performed under the following conditions.

Equipment: High Performance Liquid Chromatograph (SHIMADZU CORP.; Model LC-6A)

Column: PolyHYDROXYETHYL A, 5 μm, 9.4×200 mm (PolyC Inc.)

Mobile Phase: 50 mM formic acid

Flow rate: 0.5 ml/min

Detection: UV absorption (221 nm)

Briefly, 250 liters of water was added to 100 kg of fresh bovine erythrocytes to allow sufficient hemolysis. After adjustment of the pH to 2.8 with phosphoric acid, $2.6 \times 10^7$ units of acid protease from *Aspergillus niger* was added to the solution and reacted at 50° C. for 3 hrs.

After the above reaction, the reaction solution was heated at 80° C. for 30 min to terminate the reaction. Thereafter, an aqueous suspension of calcium hydroxide was added to the reaction solution to adjust the pH to 6.5. Then, 10 kg of diatomaceous earth was added and filtered with a filter press. The resultant filtrate was spray-dried to thereby obtain 23 kg of a globin proteolysate in a powder form.

Example 1

Fractionation and Purification of Peptides Inhibiting Elevations of TG Levels in Blood The peptide(s) of the invention were obtained through the procedures of (1) ion exchange, (2) ultrafiltration, (3) separation by reversed phase chromatography under acidic conditions, and (4) separation by reversed phase chromatography under neutral conditions.

The ratios of recovery after these procedures are shown in Table 1. The amounts of proteins were determined by the ninhydrin method.

TABLE 1

Ratios of Recovery of Adipocyte Differenciation Inhibiting Peptides from Globin Proteolysate

| Fraction | Amount of Protein (g) | Yield (%) | Method of Quantitative Determination |
| --- | --- | --- | --- |
| Globin proteolysate | 13.7 | 100 | Ninhydrin method after acid hydrolysis |
| Ion Exchange + Ultrafiltration | 4.24 | 30.9 | Ninhydrin method after acid hydrolysis |
| Reversed Phase (Acidic) Chromatography | | | |
| (1) Fraction A | 0.039 | 0.28 | Amino acid analysis after acid hydrolysis |
| (2) Fraction A' | 0.0005 | 0.004 | Amino acid analysis after acid hydrolysis |

TABLE 1-continued

Ratios of Recovery of Adipocyte Differenciation Inhibiting Peptides from Globin Proteolysate

| Fraction | Amount of Protein (g) | Yield (%) | Method of Quantitative Determination |
|---|---|---|---|
| Reversed Phase (Neutral) Chromatography | | | |
| (3) Val—Thr—Leu (Fraction B) | 0.009 | 0.06 | Amino acid analysis after acid hydrolysis |
| (4) Val—Tyr—Pro (Fraction C) | 0.006 | 0.04 | Amino acid analysis after acid hydrolysis |

(1) Ion Exchange

A 10% by weight aqueous solution of the globin proteolysate was added to a weakly acidic cation exchange resin (AMBERLITE®IRC50 (cation exchange resin), $H^+$ form; Organo) and stirred for 1 hr to allow adsorption. Then, the unadsorbed fraction was obtained.

(2) Ultrafiltration

The unadsorbed fraction obtained by ion exchange was subjected to ultrafiltration using stirring type ultrafiltration equipment ADVANTEC®; Model UHP 90K)(ultrafiltration equipment) and an ultrafiltration membrane (ADVANTEC®; UIIH-1 (ultrafiltration membrane); fraction molecular weight: 1000), and the filtrate was collected.

Figure 2:
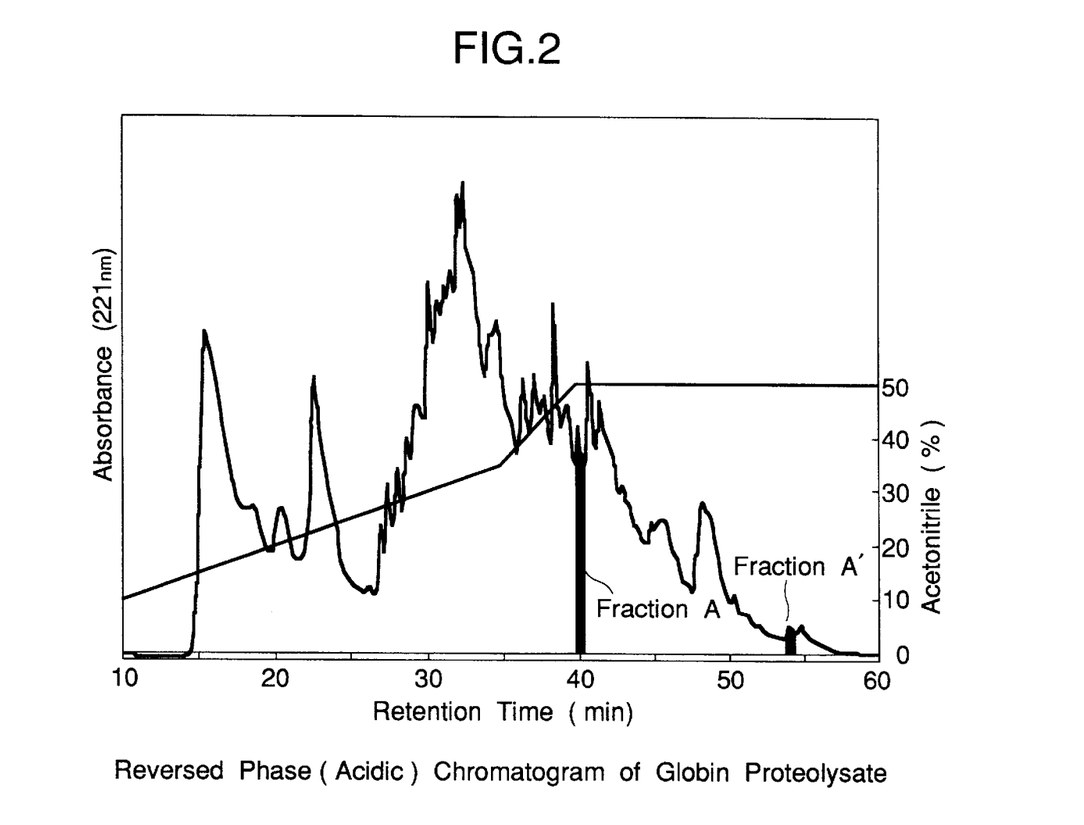
FIG. 2 is a reversed phase (acidic) chromatogram in Example 1.

(3) Reversed Phase (Acidic) Chromatograph (FIG. 2)

| | |
|---|---|
| Equipment: | High Performance Liquid Chromatograph (SHIMADZU CORP.; Model LC-10A) |
| Column: | SUPERPAC ® (high pressure chromatography column) PEP-S ® (porous silica for chromatography) 15 μm, 22.5 × 250 mm (PHARMACIA K.K.) |
| Mobile phase: | Aqueous acetonitrile solution containing 0.1% trifluoroacetic acid; Linear concentration gradient of 2–35% acetonitrile; Acetonitrile concentration was changed at a rate of 1%/min |
| Flow rate: | 5 ml/min |
| Temperature: | 40° C. |
| Detection: | UV absorption 220 nm |
| Preparative time: | Fraction A: 39.9–40.9 min Fraction A' (SEQ ID NO: 1): 53.8–54.5 min |

Figure 3:
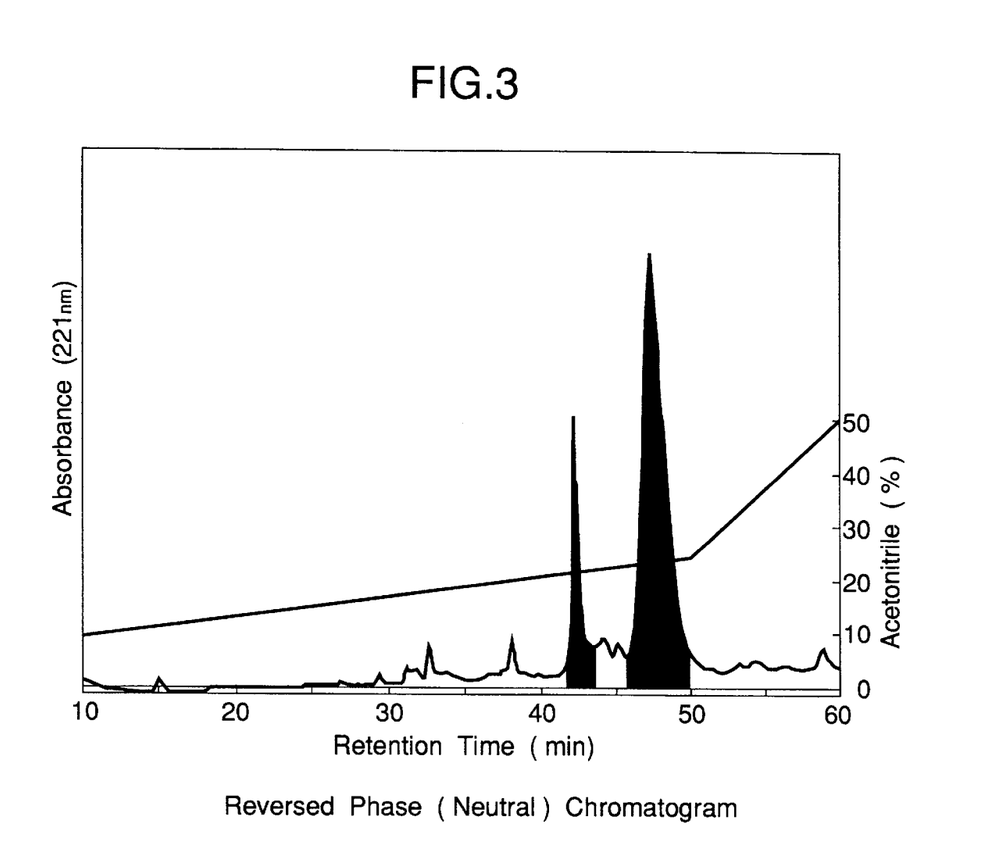
FIG. 3 is a reversed phase (neutral) chromatogram in Example 1.

(4) Reversed Phase (Neutral) Chromatography (FIG. 3)

| | |
|---|---|
| Equipment: | High Performance Liquid Chromatograph (SHIMADZU CORP., Model LC-10A) |
| Column: | SUPERPAC ® (high pressure chromatography column) PEP-S ® (porous silica for chromatography) 15 μm, 22.5 × 250 mm (PHARMACIA K.K.) |
| Mobile phase: | Aqueous acetonitrile solution containing 20 mM ammonium acetate buffer (pH 6.5); Linear concentration qradient of 0–25% acetonitrile; Acetonitrile concentration was changed at a rate of 0.5%/min |
| Flow rate: | 5 ml/min |
| Temperature: | 40° C. |
| Detection: | UV absorption (220 nm) |
| Preparative time: | Fraction B: 41.7–43.2 min (Val—Thr—Leu) Fraction C: 45.8–51.0 min (Val—Tyr—Pro) |

Example 2

Quantitative Determination of the Peptides Inhibiting Elevations of TG Concentrations in Blood Quantitative determination of those peptide fractions having an activity of inhibiting elevations of blood TG concentrations in the globin proteolysate obtained in Reference Example was performed in accordance with the purification procedures of effective peptides in Example 1.

Acid Hydrolysis

One milliliter of 6 N HCl at the final concentration was added against 3 to 5 mg of protein in a test tube, which was sealed under atmospheric pressure in the ninhydrin method and under reduced pressure for the purpose of amino acid analysis. Then, the tube was heated at 110° C. for 22 hrs.

Ninhydrin Method

The pH of the sample after hydrolysis was adjusted to 5.0 with sodium hydroxide and then the sample was reacted with a ninhydrin reagent dissolved in 0.2 M citrate buffer (pH 5.0) at 110° C. for 15 min. Absorbance at 570 nm was measured. Separately, as standard solutions, aqueous L-leucine solutions (0.75, 150, 225, 300 nmol/ml) were subjected to a ninhydrin reaction. Calibration curves were obtained from the absorbance measured, and the amount of amino groups in the sample equivalent to L-leucine was calculated.

Peptide Map

Equipment: High Performance Liquid Chromatograph (SHIMADZU CORP.; Model LC-6A)

Column: Shim-pack ISC-07/S1504 Na, 7 μm, 4.0×150 mm (SHIMADZU CORP.)

Elution solvent: Amino Acid Mobile Phase Kit (Na type) from SHIMADZU CORP.

Flow rate: 0.3 ml/min

Temperature: 55° C.

Reaction solution 1: Analysis Kit OPA Reagent from SHIMAZU CORP.

Detection: Fluorescence absorption (Ex 348 nm, Em 450 nm)

Standard Solution

As a standard solution, Amino Acid Mixed Standard Solution included 18 Components H-type (Wako Pure Chemical Industries, Ltd.) was diluted 1:25 with 0.2 M citrate buffer (pH 2.20) and 10 μl of this dilution was applied (each amino acid: 1 nmol/10 μl).

Sample Solution

The acid hydrolyzed solution was concentrated, dried and caked using a rotary evaporator, and dried further under reduced pressure for more than 12 hrs to thereby remove the HCl completely. Then, the resultant cake was dissolved in 0.2 M citrate buffer (pH 2.20) so that the content of each amino acid becomes about 100 nmol/ml. The identification of amino acids and the calculation of peak areas were performed with Chromatopack C-R4A (SHIMADZU CORP.). The amount of an amino acid was determined by comparison with that of the standard solution. The amino acid composition was calculated from ratios of individual amino acids against the total amino acid content obtained.

The results are shown as yields in Table 1 above.

Example 3

Preparation of H-Val-Thr-Leu-OH by Chemical Synthesis

H-Val-Thr-Leu-OH was synthesized with a SAM2 peptide synthesizer (Biosearch) according to the protocol of this synthesizer. Briefly, 2 g of acyloxymethyl resin to which 0.3 mmol of the 3rd protected amino acid Boc-Leu-OH was linked per gram was set in the reactor of the above peptide synthesizer, and contacted with a deblocking solution containing 45% (v/v) trifluoroacetic acid (TFA), 2.5% (v/v) anisole and 52.5% (v/v) methylene chloride (DCM) for 20 min to thereby remove the Boc group. After washing with DCM, the resin was neutralized with DCM containing 10% (v/v) diisopropylethyleneamine and further washed with DCM. Thereafter, the resin was reacted in a mixed solution of 20 ml of DCM containing 4.0 mmol each of Boc-Thr (Bz)-OH and diisopropylcarbodiimide (6.7 times the theoretical equivalent, respectively) and dimethyl formamide (DMF) for 2 hrs at room temperature. Then, the resin was washed with DMF and DCM in turn to thereby obtain Boc-Thr(Bz)-Leu-PAM resin.

According to a similar process, Boc-Val-OH was coupled.

The thus coupled protected peptide resin was reacted in anhydrous hydrogen fluoride containing 10% (v/v) anisole at 0° C. for 1 hr. Then, hydrogen fluoride was distilled off and the resin was washed with ether. From the resultant mixture of peptides and resin, peptides were extracted with 50% acetic acid and freeze-dried to thereby obtain about 250 mg of crude peptides.

The crude peptides were dissolved in 0.1% TFA and then applied on an OCTADECYL®Silica (C-18 reverse phase chromatography column) (ODS) column (Cosmosil $5C_{18}$, 250×20 mm: Nacalai Tesque) with a linear concentration gradient of acetonitrile containing 0.1% TFA (20–70%/50 min, 10 ml/min). The peptide of interest was eluted at an acetonitrile concentration of about 50%.

Example 4

Preparation of a Peptide Having the Amino Acid Sequence Shown in SEQ ID NO: 1 by Chemical Syntheisis A peptide having the amino acid sequence shown in SEQ ID NO: 1 was synthesized with the SAM2®(peptide synthesizer) described above according to the protocol of this synthesizer. Briefly, 2 g of acyloxymethyl resin to which 0.3 mmol of the 7th protected amino acid Boc-Thr(Bz)-OH was linked per gram was set in the reactor of the above peptide synthesizer, and contacted with a deblocking solution containing 45% (v/v) trifluoroacetic acid (TFA), 2.5% (v/v) anisole and 52.5% (v/v) methylene chloride (DCM) for 20 min to thereby remove the Boc group. After washing with DCM, the resin was neutralized with DCM containing 10% (v/v) diisopropylethyleneamine and further washed with DCM. Thereafter, the resin was reacted in a mixed solution of 20 ml of DCM containing 4.0 mmol each of Boc-Trp-OH and diisopropylcarbodiimide (6.7 times the theoretical equivalent, respectively) and DMF for 2 hrs at room temperature. Then, the resin was washed with DMF and DCM in turn to thereby obtain Boc-Trp-Thr(Bz)-PAM resin.

According to similar processes, Boc-Pro-OH, Boc-Tyr (BrZ)-OH, Boc-Val-OH, Boc-Val-OH and Boc-Leu-OH were coupled in this order.

Subsequently, peptides were extracted as described in Example 3 above and freeze-dried to thereby obtain about 500 mg of crude peptides. These crude peptides were developed in an ODS column as described in Example 3 above. The peptide of interest was eluted at an acetonitrile concentration of about 30%.

Example 5

Preparation of Foods Containing the Peptides of the Invention (1) Preparation of Milk Powder i. To 100 g of milk powder for infants, 0.1 g of the peptide H-Val-Thr-Leu-OH synthesized in Example 3 above was added to thereby prepare a milk powder having a function of inhibiting elevations of TG levels in blood.

ii. To 100 g of milk powder for infants, 0.1 g of the peptide having the amino acid sequence shown in SEQ ID NO: 1 synthesized in Example 4 above was added to thereby prepare a milk powder having a function of inhibiting elevations of TG levels in blood.

(2) Preparation of Chocolate i. To 100 g of chocolate, 0.5 g of the peptide H-Val-Thr-Leu-OH synthesized in Example 3 above was added to thereby prepare a chocolate having a function of inhibiting elevations of TG levels in blood.

ii. To 100 g of chocolate, 0.5 g of the peptide having the amino acid sequence shown in SEQ ID NO: 1 synthesized in Example 4 was added to thereby prepare a chocolate having a function of inhibiting elevations of TG levels in blood.

Example 6

Preparation of a Feed Containing the Peptide(s) of the Invention

The peptide H-Val-Thr-Leu-OH synthesized in Example 3 and the peptide having the amino acid sequence shown in SEQ ID NO: 1 were individually added to a premix containing vitamins, minerals, etc. at a rate of 1% by weight. Each of the resultant premixes was added to a commercial feed for hatchery fish at a rate of 10% by weight to thereby prepare a feed for hatchery fish having a function of inhibiting elevations of TG levels in blood.

Test Example 1

Effect (in vivo) of the Chemically Synthesized Agents for Inhibiting Elevations of TG Levels in blood Serum TG elevation inhibiting action at the time of in vivo lipid loading was examined on the three peptides of the invention inhibiting elevations of TG levels in blood (i.e., the peptide having the amino acid sequence of SEQ ID NO: 1 and the peptides Val-Thr-Leu and Val-Tyr-Pro synthesized by the method described in Example 4). Healthy albino mice (5–10 weeks old; body weight: about 20–30 g) were used in this experiment. To each mouse, 250 mg of olive oil and an aqueous solution of the above peptide were administered orally. Three hours thereafter, blood was collected under anesthesia with Nembutal. After separation of the blood, the TG level in blood was determined. The results are shown in Table 2.

TABLE 2

Determination of TG Levels in Blood

Ratio of Increase in Blood TG Levels (%)

| Dose (mg/mouse) | Proteolysate | Val—Tyr—Pro | Val—Thr—Leu | SEQ ID NO: 1 |
|---|---|---|---|---|
| $4 \times 10^{-5}$ | | | | 14 |
| $1 \times 10^{-4}$ | | | | 33 |
| $4 \times 10^{-4}$ | | | | 33 |
| $1 \times 10^{-3}$ | | | | 65 |
| 0.1 | | 39 | 30 | |
| 0.2 | | 50 | 33 | |
| 1.0 | | 50 | 73 | |
| 2.5 | | 69 | 76 | |
| 5.0 | | 79 | 79 | |
| 20 | 40 | | | |
| 40 | 55 | | | |

TABLE 2-continued

Determination of TG Levels in Blood

Ratio of Increase in Blood TG Levels (%)

| Dose (mg/mouse) | Proteolysate | Val—Tyr—Pro | Val—Thr—Leu | SEQ ID NO: 1 |
|---|---|---|---|---|
| 60 | 82 | | | |
| 80 | 86 | | | |
| $ID^{50}$ *1 | 28 | 0.34 | 0.43 | $5.6 \times 10^{-4}$ |
| Specific Activity | 1 | 82 | 65 | 50000 |

*1 Dose (mg/mouse) exhibiting 50% inhibition.

As a result, all of the three peptides of the invention inhibited elevations of TG levels in blood. In particular, the peptide having the amino acid sequence shown in SEQ ID NO: 1 exhibited a specific activity 50000 times as higher as that of the proteolysate peptide. On the other hand, though specific activities of the other two peptides were about 1/100 compared to the peptide of SEQ ID NO: 1, they had specific activities more than 50 times that of the proteolysate peptide.

Test Example 2

Safety Test of the Peptides of the Invention

The peptides of the invention (i.e., the peptide having the amino acid sequence of SEQ ID NO: 1 and the peptides Val-Thr-Leu and Val-Tyr-Pro) were administered orally to ICR male and female mice at a dose of 10 g/kg body weight or more (maximum possible dose) in various ratios (0:1, 1:1, 1:0). As a result, no death occurred.

Industrial Applicability

According to the present invention, a peptide inhibiting elevations of triglyceride levels in blood; an agent for inhibiting elevations of triglyceride levels in blood comprising the peptide as an active component; a food for specified health use (the so-called physiologically functional food) endowed with a function of inhibiting elevations of triglyceride levels in blood; and a feed endowed with a function of inhibiting elevations of triglyceride levels in blood are obtained.

According to the present invention, it becomes possible to prevent or treat human or animal obesity and hyperlipemia, and cardiovascular such as hypertension and arteriosclerosis associated therewith. Furthermore, it becomes possible to improve the meat quality of livestock and hatchery fish.

We claim:

1. A pharmaceutical composition for administration to a human or an animal comprising a peptide consisting of Val-Thr-Leu as an active component.

2. The pharmaceutical composition of claim 1 being selected from the group consisting of tablets, powder, granules, pills and injectable form.

3. The pharmaceutical composition of claim 2 which is an injectable form.

4. The pharmaceutical composition of claim 3 wherein said injectable form is selected from the group consisting of solutions, suspensions and emulsions.

5. The pharmaceutical composition of claim 3 wherein said injectable form may be administered by intravenous, intramuscular, subcutaneous, intracutaneous and intraperitoneal administration.

6. The pharmaceutical composition of claim 1 comprising from about 1 to about 100 mg of said pharmaceutical composition.

7. A food composition for administration to a human or an animal comprising a peptide consisting of Val-Thr-Leu as an active component.

8. A feed composition for administration to an animal comprising a peptide consisting of Val-Thr-Leu as an active component.

9. A method of inhibiting elevated triglyceride levels in the blood of a human or animal comprising administering an effective amount of a pharmaceutical composition comprising a peptide consisting of the amino acid sequence shown in SEQ ID NO;1 or said peptide in combination with a peptide consisting of Val-Tyr-Pro and/or a peptide consisting of Val-Thr-Leu as an active component(s) to said human or animal.

10. A method of inhibiting elevated triglyceride levels in the blood of a human comprising said human ingesting an effective amount of a food composition comprising a peptide consisting of the amino acid sequence shown in SEQ ID NO: 1 or said peptide in combination with a peptide consisting of Val-Tyr-Pro and/or a peptide consisting of Val-Thr-Leu as an active component(s).

11. A method of inhibiting elevated triglyceride levels in the blood of an animal comprising said animal ingesting an effective amount of the feed composition comprising a peptide consisting of the amino acid sequence shown in SEQ ID NO: 1 or said peptide in combination with a peptide consisting of Val-Tyr-Pro and/or a peptide consisting of Val-Thr-Leu as an active component(s).

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Bos frontalis

<400> SEQUENCE: 1

Leu Val Val Tyr Pro Trp Thr
 1               5